United States Patent
Joo et al.

(10) Patent No.: US 12,215,346 B2
(45) Date of Patent: Feb. 4, 2025

(54) METHOD FOR ISOLATING AND CULTURING NEURAL STEM CELLS WITH HIGH EFFICIENCY

(71) Applicant: MEDINNO INC., Gyeonggi-do (KR)

(72) Inventors: Kyeung Min Joo, Seoul (KR); Hyun Nam, Gyeonggi-do (KR)

(73) Assignee: MEDINNO INC., Gyeonggi-do (KR)

( * ) Notice: Subject to any disclaimer, the term of this patent is extended or adjusted under 35 U.S.C. 154(b) by 978 days.

(21) Appl. No.: 16/980,889

(22) PCT Filed: Jan. 30, 2019

(86) PCT No.: PCT/KR2019/001288
§ 371 (c)(1),
(2) Date: Sep. 15, 2020

(87) PCT Pub. No.: WO2019/177270
PCT Pub. Date: Sep. 19, 2019

(65) Prior Publication Data
US 2022/0243175 A1 Aug. 4, 2022

(30) Foreign Application Priority Data

Mar. 16, 2018 (KR) ......................... 10-2018-0031101
Jan. 29, 2019 (KR) ......................... 10-2019-0011226

(51) Int. Cl.
| | | |
|---|---|---|
| C12N 5/0797 | (2010.01) | |
| C12N 9/22 | (2006.01) | |
| C12N 9/50 | (2006.01) | |
| G01N 1/40 | (2006.01) | |

(52) U.S. Cl.
CPC ............. *C12N 5/0623* (2013.01); *C12N 9/22* (2013.01); *C12N 9/63* (2013.01); *C12Y 301/21001* (2013.01); *C12Y 304/22002* (2013.01); *G01N 1/4044* (2013.01); *C12N 2509/00* (2013.01)

(58) Field of Classification Search
None
See application file for complete search history.

(56) References Cited

U.S. PATENT DOCUMENTS

| | | |
|---|---|---|
| 2012/0135016 A1 | 5/2012 | Eisenbach-Schwartz et al. |
| 2012/0295348 A1* | 11/2012 | Nam ........................ A61P 25/00 435/325 |
| 2019/0374681 A1* | 12/2019 | Joo ...................... C12N 5/0619 |

FOREIGN PATENT DOCUMENTS

| | | |
|---|---|---|
| JP | 2007504808 A | 3/2007 |
| KR | 20110090810 A | 8/2011 |
| KR | 101269125 | 6/2013 |
| WO | 2003064601 | 1/2003 |
| WO | 2003089631 | 10/2003 |
| WO | 2007020611 | 2/2007 |

OTHER PUBLICATIONS

Pertoft, Hakan. Fractionation of cells and subcellular particles with Percoll. Elsevier. J. Biochem. Biophys. Methods 44 (2000) pp. 1-30. (Year: 2000).*
Fischer, J. et al., "Prospective isolation of adult neural stem cells from the mouse subependymal zone", Nat. Protoc., Nov. 17, 2011, vol. 6(12), pp. 1981-1989 (Year: 2011).*
Mothe et al., 2015, "Isolation of Neural Stem, Progenitor Cells from the Periventricular Region of the Adult Rat and Human Spinal Cord", Journal of Visualized Experiments, 99:1-8.
Nam et al., 2015, "Adult human neural stem cell therapeutics", World Journal of Stem Cell, 7:126-136.
Japanese Office Action for Japanese Patent Application No. 2020-549677.
Extended European Search Report for European Patent Application No. 19767415.3.
Negishi et al., 2002, "Cryopreservation of Brain Tissue for Primary Culture", Exp. Anim., 51:383-390.
Fischer, J. et al., "Prospective isolation of adult neural stem cells from the mouse subependymal zone", Nat. Protoc., Nov. 17, 2011, vol. 6(12), pp. 1981-1989.
Lopez-Ramirez, M. A. et al., "Isolation and Culture of Adult Zebrafish Brain-derived Neurospheres", J. Vis. Exp., Feb. 29, 2016, vol. 108, e53617, pp. 1-10.

* cited by examiner

*Primary Examiner* — Nghi V Nguyen
(74) *Attorney, Agent, or Firm* — Riverside Law LLP (57) ABSTRACT

The present invention relates to a method for isolating and culturing neural stem cells with high efficiency, which may shorten the time for isolation and culture by simplifying a method for isolating and culturing neural stem cells and may increase the acquisition yield of neural stem cells. The present invention provides a method for isolating and culturing neural stem cells with high efficiency, comprising the steps of adding brain tissue into an enzyme solution so as to subject the brain tissue to enzyme treatment; physically isolating cell clumps from the enzyme treated brain tissue by dividing the cell clumps according to size and removing impurities; and inoculating the cell clumps on a culture dish so as to subculture.

3 Claims, 15 Drawing Sheets

METHOD FOR ISOLATING AND CULTURING NEURAL STEM CELLS WITH HIGH EFFICIENCY

CROSS-REFERENCE TO RELATED APPLICATIONS

This application is the U.S. national phase application filed under 35 U.S.C. § 371 claiming benefit to International Patent Application No. PCT/KR2019/001288, filed on Jan. 30, 2019, which claims priority to Korean Patent Application No. 10-2018-0031101, filed Mar. 16, 2018, and Korean Patent Application No. 10-2019-0011226, filed Jan. 29, 2019, the disclosures of which are incorporated herein by reference in their entirety.

TECHNICAL FIELD

The present invention relates to a method for isolating and culturing neural stem cells with high efficiency, which is able to shorten an isolation and culture time by simplifying a method of isolating and culturing neural stem cells, and increase the acquisition yield of neural stem cells.

BACKGROUND ART

Biotechnology for the $21^{st}$ century has suggested the possibility of new solutions to food, environmental and health problems with human welfare as the final goal, and recently, technology using stem cells is emerging as a new chapter in treatment of incurable diseases. Previously, organ transplantation or gene therapy was suggested to treat human incurable diseases, but was not effectively put to practical use because of rejection, shortages in supply of organs, poor delivery of vector or lack of adequate therapeutic genes.

Accordingly, with the growing interest in stem cell research, it was recognized that pluripotent stem cells capable of forming all organs through proliferation and differentiation can fundamentally solve organ damage as well as treat many incurable diseases. Stem cells refer to cells that can differentiate into two or more types of cells with self-renewability, and classified into totipotent stem cells, pluripotent stem cells and multipotent stem cells. Many scientists have suggested the applicability of stem cells in various ways including the treatment of incurable diseases such as Parkinson's disease, various types of cancer, diabetes and spinal cord injury, as well as regeneration of almost all human organs.

Neural stem cells, that is stem cells that can differentiate into neurons, astrocytes and oligodendrocytes, were first found in the rodent, mice. Afterward, it was known that neural stem cells are present in the human brain, and involved in brain regeneration throughout one's life. Therefore, for treatment of degenerative neurological diseases, recently, the development of a therapeutic agent using neural stem cells is attracting attention.

In the beginning of human neural stem cell research, neural stem cells were isolated from a fetal brain and cultured. Based on those researches, recently, clinical trials for treating stroke or spinal cord injury have been conducted. In addition, research on isolating and culturing neural stem cells from embryonic stem cells has been undertaken. Recently, a method for differentiation into neural stem cells from induced pluripotent stem (iPS) cells has been studied, and there is an increasing expectation of culture of neural stem cells that enable autologous transplantation.

However, neural stem cells derived from a fetus or embryonic stem cells have ethical problems and concerns about tumorigenic safety. In addition, since iPS cell-derived neural stem cells also have problems with tumorigenic safety, for clinical application of these stem cells, there was a need for verification of biological safety.

In previous research, for isolation and culture of neural stem cells, a method for isolating and culturing single cells from brain tissue has been widely used.

However, a method of isolating and culturing neural stem cells, which includes single cell isolation using Percoll® took a long time, and has a problem with the acquisition yield of neural stem cells.

DISCLOSURE

Technical Problem

The present invention provides a method for isolating and culturing neural stem cells with high efficiency, which is able to shorten an isolation and culture time by simplifying a method of isolating and culturing neural stem cells, and increase the acquisition yield of neural stem cells.

However, technical problems to be solved in the present invention are not limited to the above-described problems, and other problems which are not described herein will be fully understood by those of ordinary skill in the art from the following descriptions.

Technical Solution

In one aspect, the present invention provides a method for isolating and culturing neural stem cells with high efficiency, which includes: placing brain tissue in an enzyme solution for enzyme treatment; physically dissociating cell clumps from enzyme-treated brain tissue; separating the cell clumps by size and removing impurities; and performing subculture by seeding the cell clumps in a culture dish.

In addition, the enzyme solution may include papain; DNase I; and D, L-cysteine.

In addition, the cell clumps may have a size of 40 to 70 μm, or 70 to 100 μm.

In addition, the brain tissue may be adult brain tissue, and the method for isolating and culturing neural stem cells may not include single cell isolation using Percoll®.

Advantageous Effects

A method for isolating and culturing neural stem cells with high efficiency according to the present invention can shorten an isolation and culture time by simplifying a method of isolating and culturing neural stem cells, and increase the acquisition yield of neural stem cells. In addition, cell viability can be increased by shortening of an isolation and culture time, and a large number of cells can be acquired in a short time, thereby having an advantage of increasing the success rate of culturing neural stem cells.

MODES OF THE INVENTION

The present invention is directed to providing a method for isolating and culturing neural stem cells with high efficiency, which is able to shorten an isolation and culture time by simplifying a method of isolating and culturing neural stem cells, and increase the acquisition yield of neural stem cells.

In one embodiment of the present invention, as a result of culturing neural stem cells according to the method of the present invention (clump culture), compared with using conventional Percoll® method, it is confirmed that more neural stem cells per the same brain tissue weight may be obtained (see Example 1).

In another embodiment of the present invention, it is confirmed that the neural stem cells according to the method of the present invention (clump culture) maintain neural differentiation ability (see Example 3).

In still another embodiment of the present invention, as a result of separating and culturing clumps by size, it is confirmed that Clump type II (70 to 100 μm) exhibits the best result of the acquisition efficiency of neural stem cells (see Examples 4 and 5).

In yet another embodiment of the present invention, when Clump type II is cultured according to the method of the present invention (clump culture), it is confirmed that the time for first subculture is shortened, a cell morphology is normal, neural differentiation ability is also normal, and thus stem cell properties are well maintained (see Example 6).

In yet another embodiment of the present invention, it is confirmed that neural stem cells derived from Clump type II have angiogenic ability (see Example 7).

Hereinafter, the present invention will be described in detail.

The present invention provides a method for isolating and culturing neural stem cells with high efficiency, which includes: placing brain tissue in an enzyme solution for enzyme treatment; physically dissociating cell clumps from enzyme-treated brain tissue; separating the cell clumps by size and removing impurities; and performing subculture by seeding the cell clumps in a culture dish.

The method of isolating and culturing neural stem cells, including isolating single cells using Percoll® takes a long time, and has a problem in the acquisition yield of neural stem cells. Therefore, the inventors confirmed through an experiment, in the case of introducing a process of separating the cells by clumps and not including a process of isolating single cells using Percoll®, an isolation and culture time was shortened, and the acquisition yield of neural stem cells was able to increase, and thus the present invention was completed.

According to one aspect of the present invention, a method for isolating and culturing neural stem cells with high efficiency, which includes: placing brain tissue in an enzyme solution for enzyme treatment; physically dissociating cell clumps from enzyme-treated brain tissue; separating the cell clumps by size and removing impurities; and performing subculture by seeding the cell clumps in a culture dish, is provided.

The enzyme solution is not particularly limited, and may include papain; DNase I; and D, L-cysteine.

In addition, after dissociation from brain tissue, the cell clumps may be further separated by size using a mesh. The cell clumps may have a size of 40 to 70 μm, or 70 to 100 μm.

Moreover, the brain tissue is preferably adult brain tissue.

Meanwhile, as described above, the method for isolating and culturing neural stem cells with high efficiency according to the present invention does not include isolating single cells using Percoll®. The method for isolating and culturing neural stem cells according to the present invention has advantages of shortening an isolation and culture time by simplifying a method for isolating and culturing neural stem cells by excluding single cell isolation using Percoll®, increasing the acquisition yield of neural stem cells, increasing cell viability due to the shortening of an isolation and culture time, and acquiring a large number of cells in a short time, thereby increasing the success rate of culturing neural stem cells.

Hereinafter, to help understanding the present invention, exemplary examples will be suggested. However, the following examples are merely provided to more easily understand the present invention, and not to limit the present invention.

EXAMPLES

Example 1. Primary Culture of Neural Stem Cells

After measuring the weight of human brain tissue, washing was performed two to three times using phosphatebuffered saline (PBS). Following homogenization of the tissue to an appropriate size, the tissue was added to an enzyme solution (10 units/ml of papain, 0.1 µmg/ml of DNase I and 4 µmg/ml of D, L-cysteine), and then physically cut into smaller fragments using a blade and surgical scissors. After thirty minutes of treatment at 37° C., the resulting fragments were disrupted using a disposable pipette, filtered using a 70 µm mesh, and washing was then performed using PBS.

When Percoll® was used, a Percoll® solution was prepared by mixing 10-fold concentrated PBS and Percoll® in a ratio of 1:9, 20 µmL of a cell suspension and 10 µmL of Percoll® solution were mixed and centrifuged at 20,000 rpm and 18° C. to isolate cells from a cell layer, and the cells were then washed twice with PBS again, and cultured in a poly-L-ornithine (PLO)-coated dish.

When reaching a confluency of 70 to 80%, the cells were detached using Accutase, and then subcultured. The number of cells and viability were calculated using a Tryphan Blue solution and a population doubling length (PDL) was measured, thereby plotting a cell growth curve, and morphologies of the isolated and cultured neural stem cells were observed under a microscope.

Figure 1:
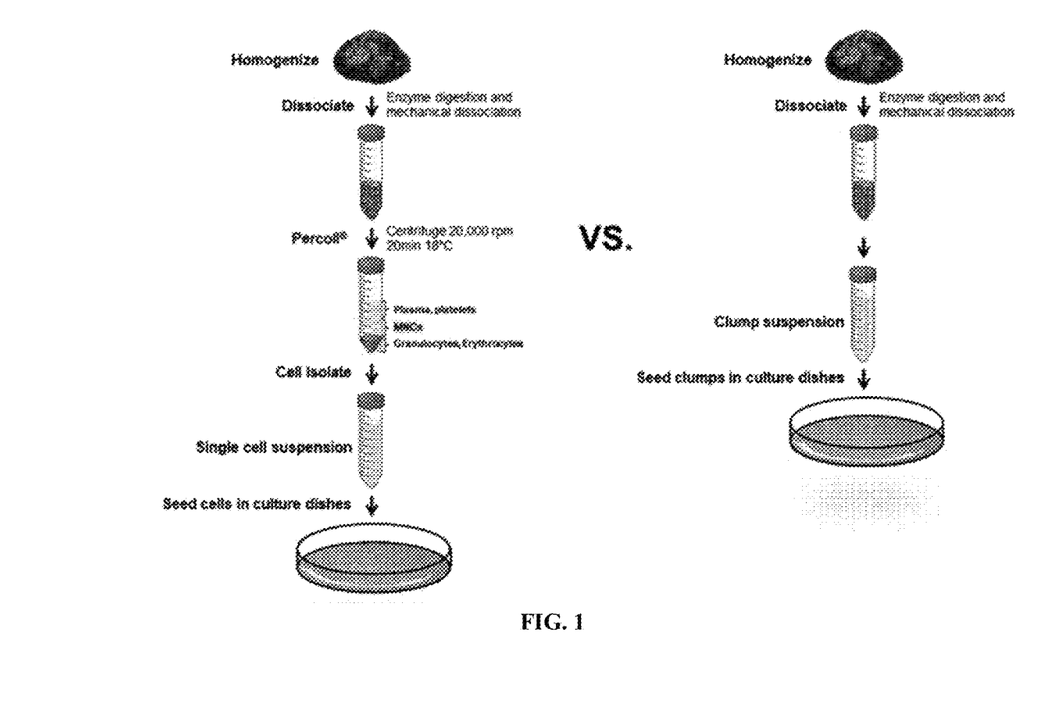
FIG. 1 shows schematic diagrams of a conventional method for isolating and culturing neural stem cells using Percoll®, and clump culture, which is an isolation and culture method according to the present invention.
Figure 2A:
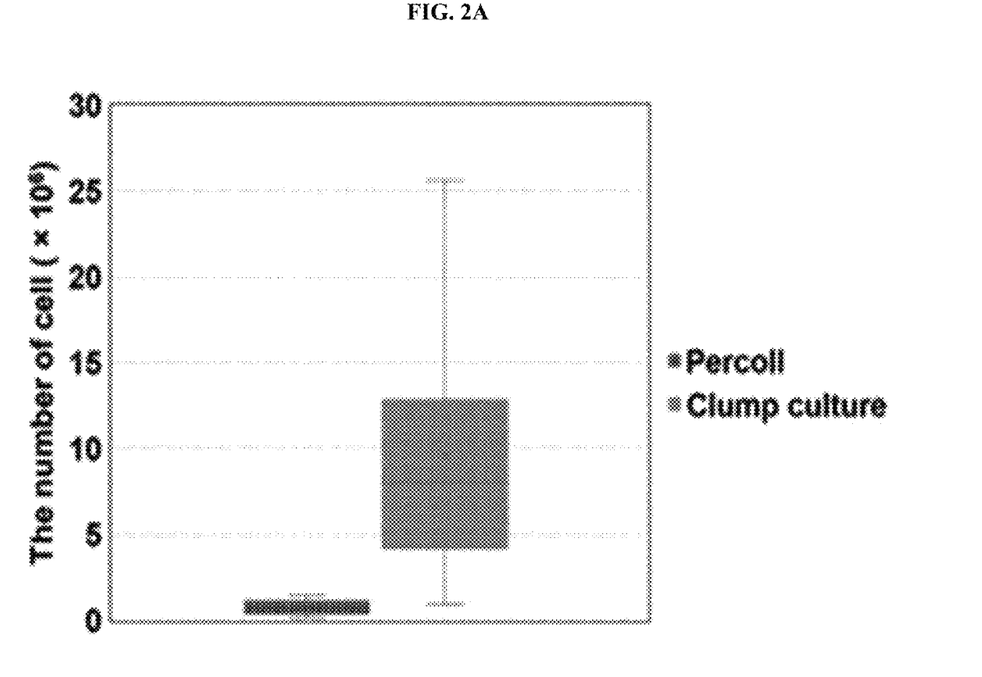
FIG. 2A is a graph of comparing a cell yield per brain tissue weight (g) between the conventional isolation and culture method (Percoll®) and the isolation and culture method (clump culture) according to one aspect of the present invention.
Figure 2B:
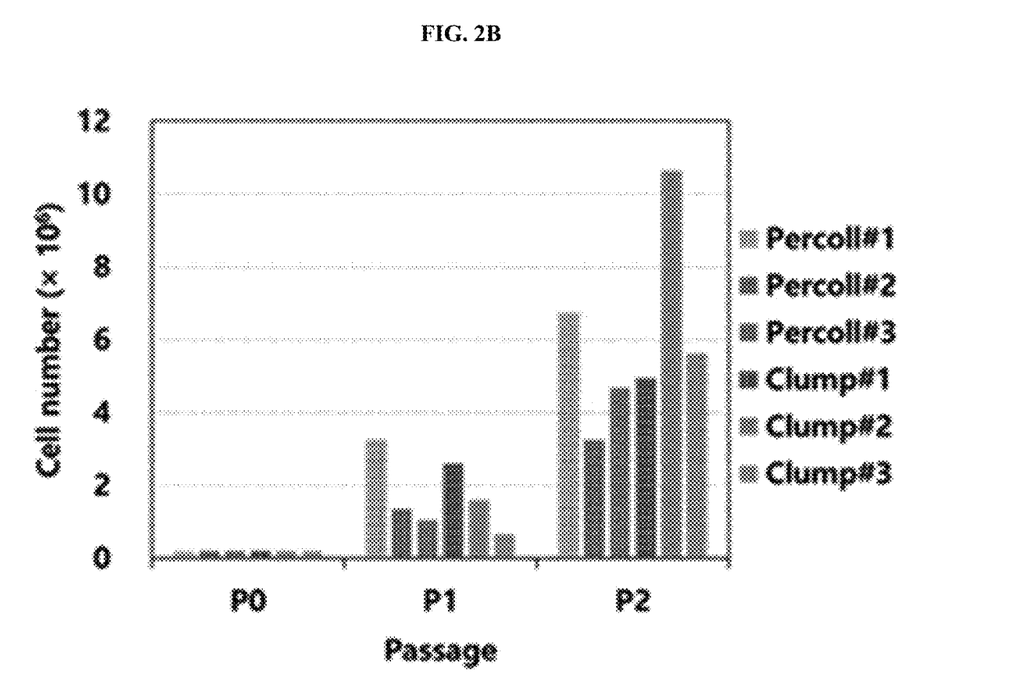
FIG. 2B is a graph showing cell growth according to subculture of neural stem cells acquired according to the conventional isolation and culture method (Percoll®) and the isolation and culture method (clump culture) according to one aspect of the present invention.

As a result, as shown in FIG. 2A, according to the isolation and culture method (clump culture), it was confirmed that a larger amount of neural stem cells per the same weight of brain tissue, compared with a method using Percoll®, may be acquired, and as shown in FIG. 2B, according to the isolation and culture method (clump culture), it was confirmed that a cell growth is overall superior to that according to the conventional method using Percoll®.

Figure 3A:
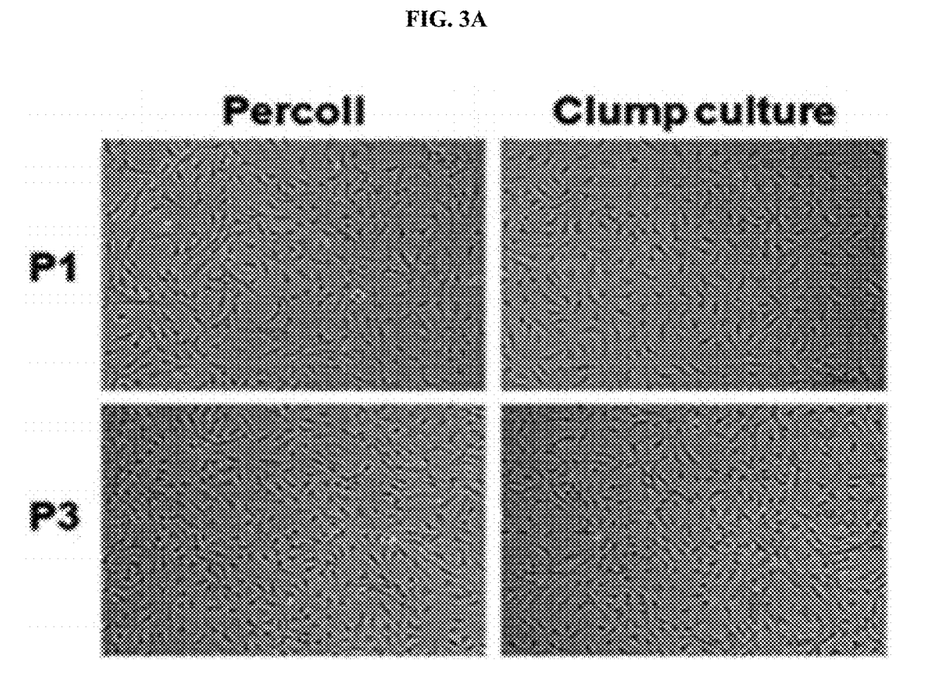
FIG. 3A shows the morphologies of neural stem cells according to the conventional isolation and culture method (Percoll®) and the isolation and culture method (clump culture) according to one aspect of the present invention.

In addition, as shown in FIG. 3A, as a result of observing the cultured cells, it was also confirmed that cell morphologies of the isolation and culture method according to the present invention (clump culture), are similar to those of the conventional method using Percoll®.

Example 2. Induction of Differentiation Under Neural Differentiation Condition Neural stem cells were cultured to be a confluency of approximately 70 to 80%, and washed twice with PBS. Forty-eight hours after incubation under neural differentiation conditions such as DMEM/F12, 0.5% FBS, B27, 0.5 µmM IBMX and P/S, the cells were fixed, followed by immunofluorescence staining.

Example 3. Immunostaining

Neural stem cells were cultured on a PLO-coated 8-well slide chamber (Thermo) and fixed in 4% paraformaldehyde for 5 µminutes. The cells were rinsed with 0.1% Triton-X 100-diluted PBS (0.1% PBST), treated with a blocking solution (5% normal goat serum and 5% normal donkey serum) for approximately 1 hour, and reacted overnight with a primary antibody. At next day, cells were washed twice with PBS, and treated with an Alexa488 or Alexa594-conjugated secondary antibody for 1 hour. After counter staining with DAPI and mounting, the cells were observed under a fluorescence microscope.

Figure 3B:
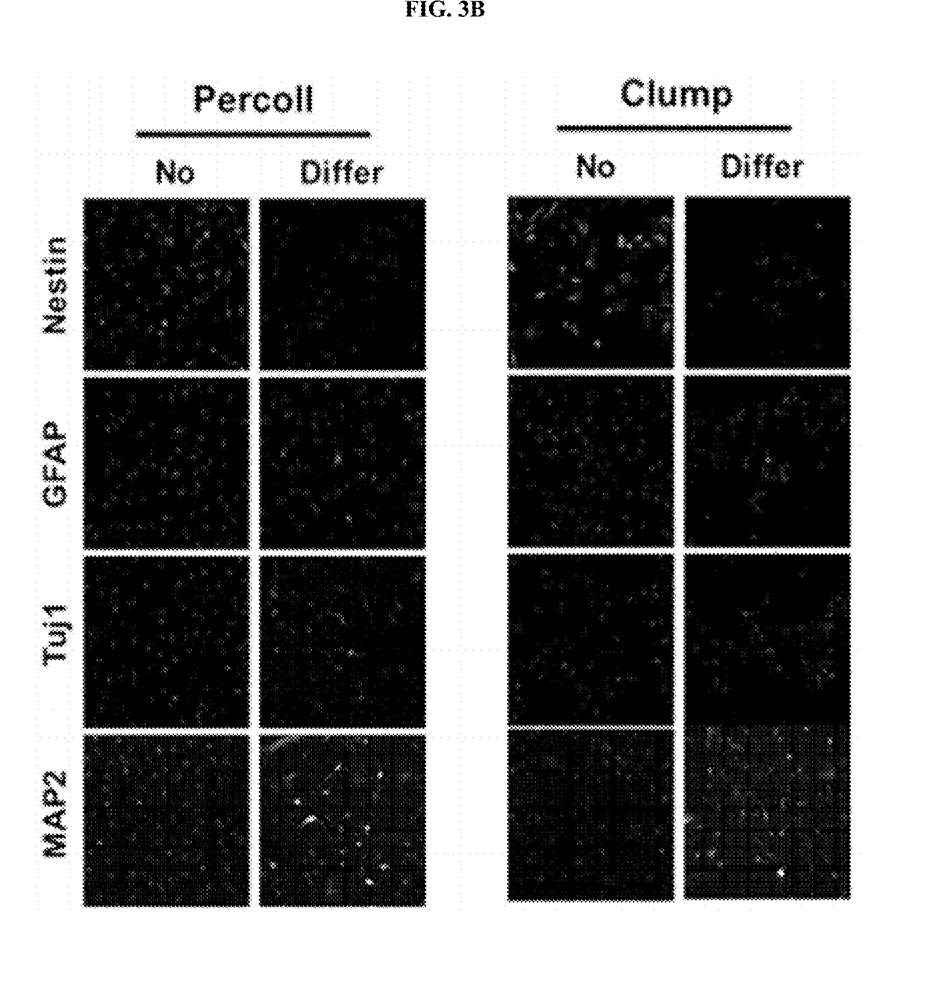
FIG. 3B shows differentiation patterns under differentiation conditions for neural stem cells isolated and incubated according to the conventional isolation and culture method (Percoll®) and the isolation and culture method (clump culture) according to one aspect of the present invention.

As a result, as shown in FIG. 3B, after differentiation of neural stem cells, it was confirmed that the expression of Nestin decreased and the expression of neuronal cells (Tuj 1, MAP2) and astrocytes (GFAP) increased.

Example 4. Size-Dependent Separation of Clumps and their Morphologies

Figure 4A:
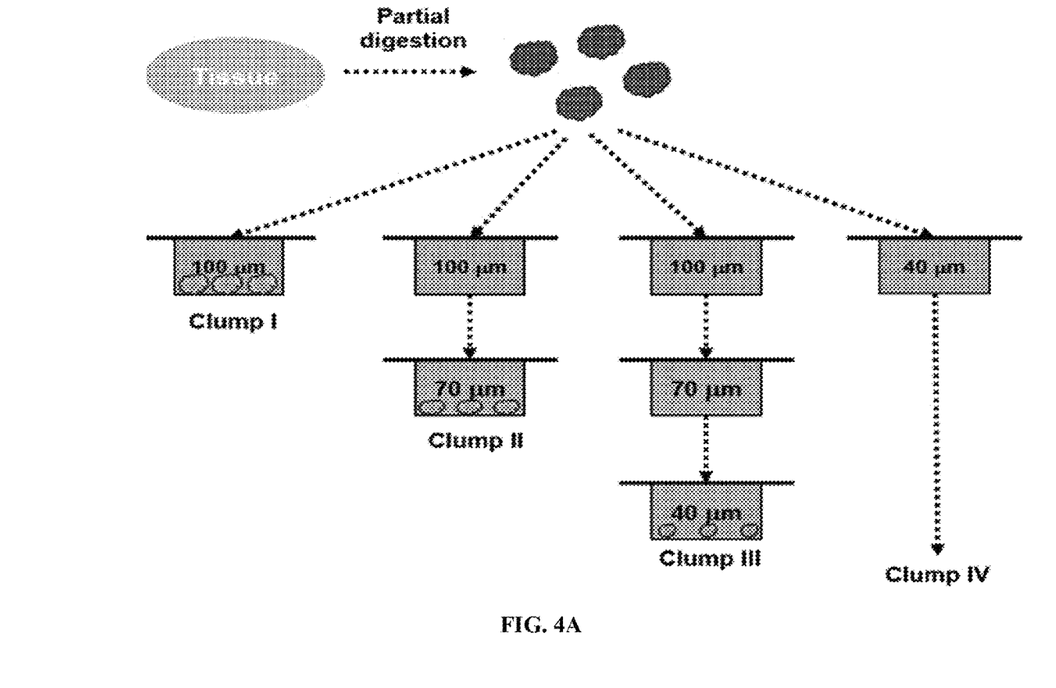
FIG. 4A simply illustrates a method of separating clumps to find the optimal size of clumps for the clump culture method.

To find the optimal condition for a clump culture method, human brain tissue was treated with an enzyme solution, physically dissociated, and then filtered through various sizes of meshes, thereby separated clumps with specific rages of size (see FIG. 4A). The clumps were classified as type 1 to IV by size as shown below, and then observed under a microscope.

Figure 4B:
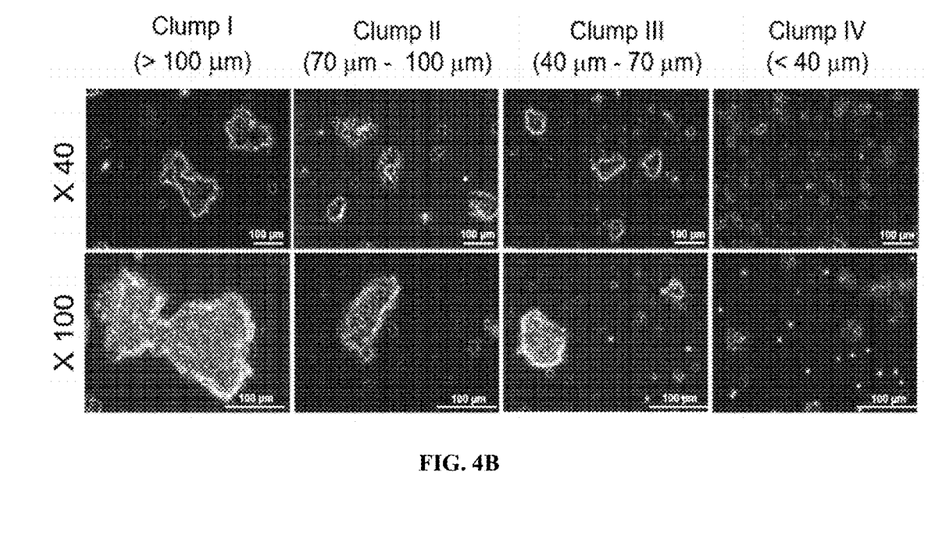
FIG. 4B shows the morphologies of four groups of clumps (Clump I to IV), observed using a microscope.

Clump type I>100 µm
70 µm<Clump type II<100 µm
40 µm<Clump type III<70 µm
Clump type IV<40 µm As a result, as shown in FIG. 4B, separation into each type of clumps with uniform size was confirmed.

Example 5. Comparison of Efficiency in Separation and Culture of Clump Types I to IV To compare isolation and culture efficiencies among Clump types I to IV, each type of clumps derived from two patients according to the method of Example 1 were cultured to confirm the number of colonies and observe colony morphology using a microscope.

Figure 5A:
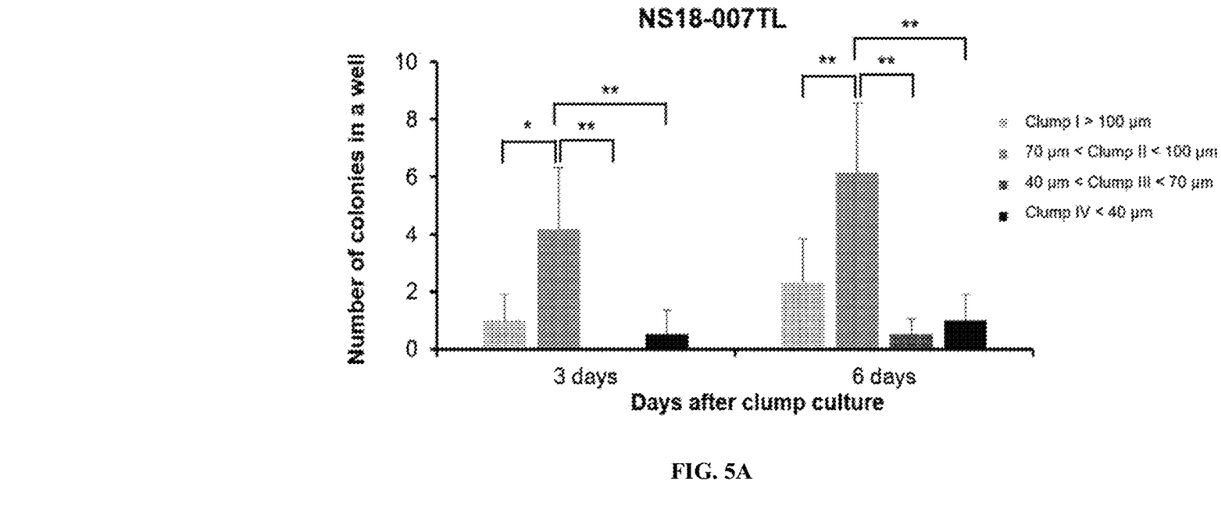
FIGS. 5A and 5B show the numbers of colonies observed on the bottom of a culture dish three days and six days after seeding Clump type I to IV derived from two patients (NS18-007TL and NS18-008TL).
Figure 5B:
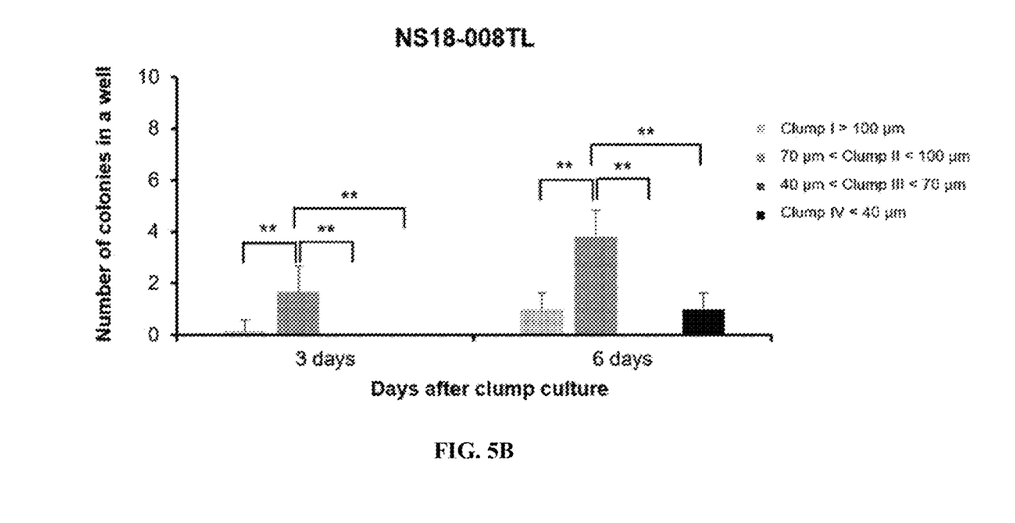
Figure 5C:
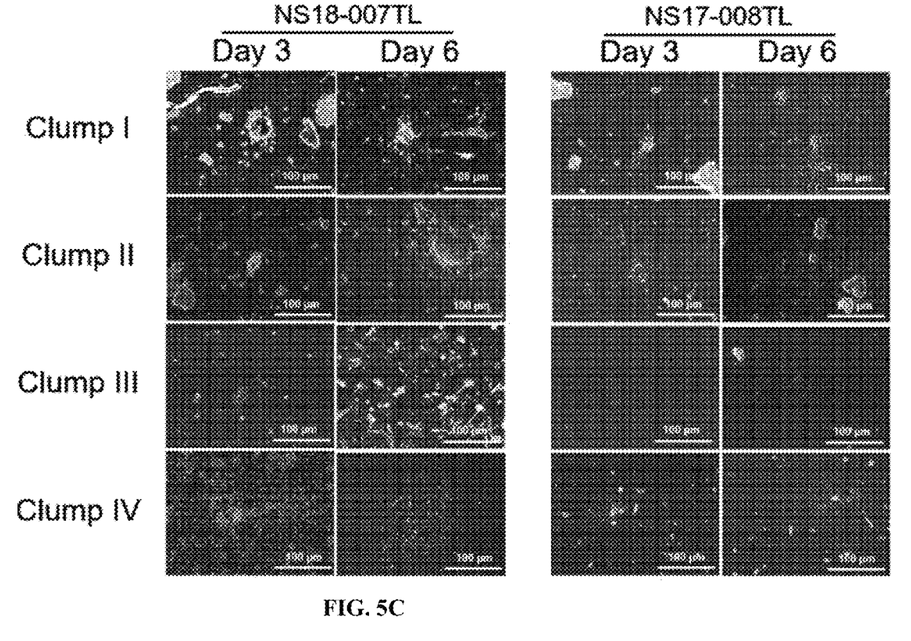
FIG. 5C shows the morphologies of colonies observed in culture dishes three days and six days after seeding Clump type I to IV.

As a result, as shown in FIGS. 5A and 5B, on both day 3 and day 6 of isolation and culture, the largest number of colonies were observed in Clump type II, confirming that the Clump type II has the best culture efficiency.

Example 6. Confirmation of Culture Time for Subculture and Neural Differentiation Ability of Clump Type II To compare efficiencies between the case of culturing Clump type II by the method according to the present invention and the case of culturing single cells using Percoll®, cells were cultured according to the method of Example 1 and then a growth curve was plotted, followed by observation of the morphologies of cells derived from Clump type II using a microscope.

In addition, to confirm whether neural stem cells derived from the Clump type II method maintain neural differentiation ability, after neural differentiation, immunofluorescence staining was used according to the method of Example 3.

Figure 6A:
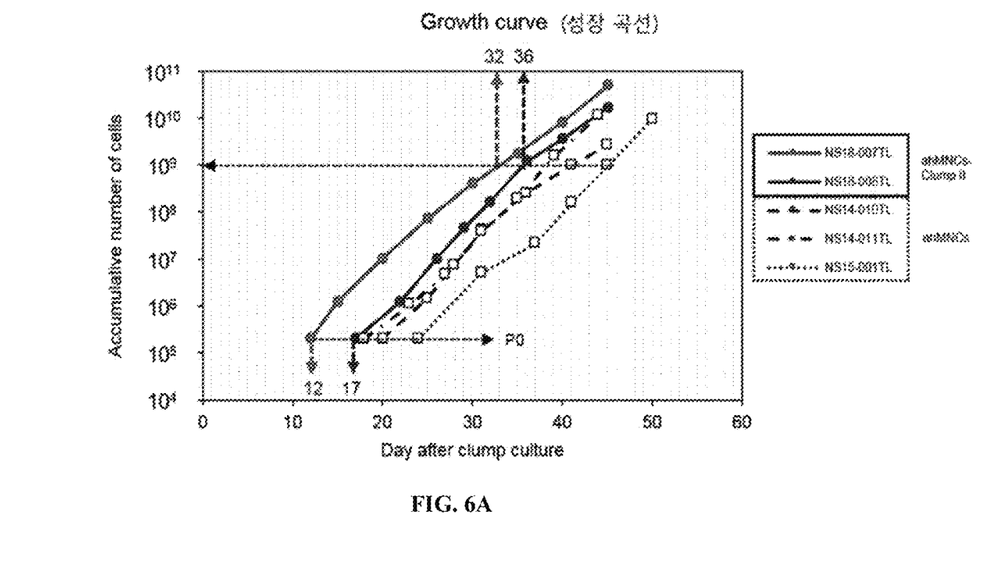
FIG. 6A is a graph of comparing the growth of cells cultured using Clump type II and the growth of single cells isolated using conventional Percoll® method.
Figure 6B:
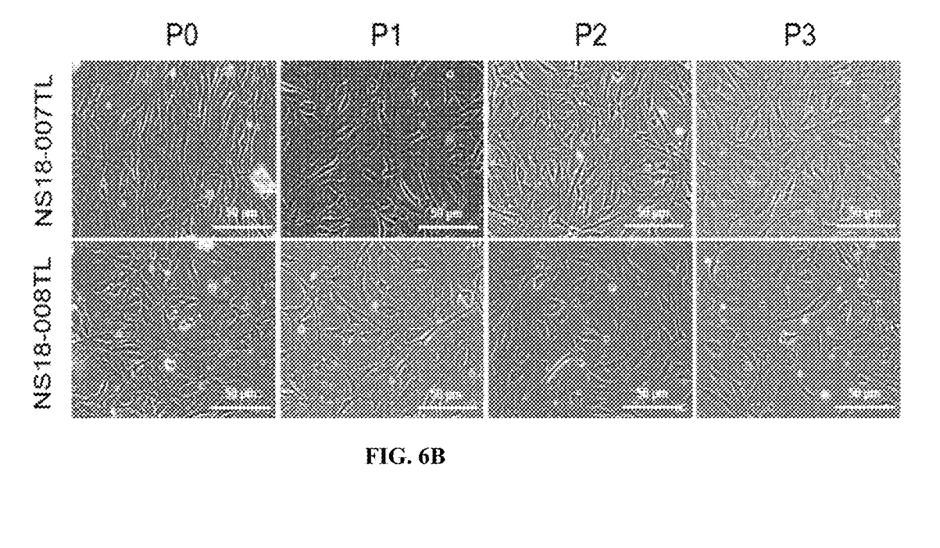
FIG. 6B shows cell morphologies during subculture of Clump type II.

As a result, as shown in FIG. 6A, it was confirmed that, in the case of Clump type II, the time for first subculture was shortened, the time to reach $10^9$ cells was also shortened, and as shown in FIG. 6B, cell morphology was well maintained in subculture of Clump type II.

Figure 6C:
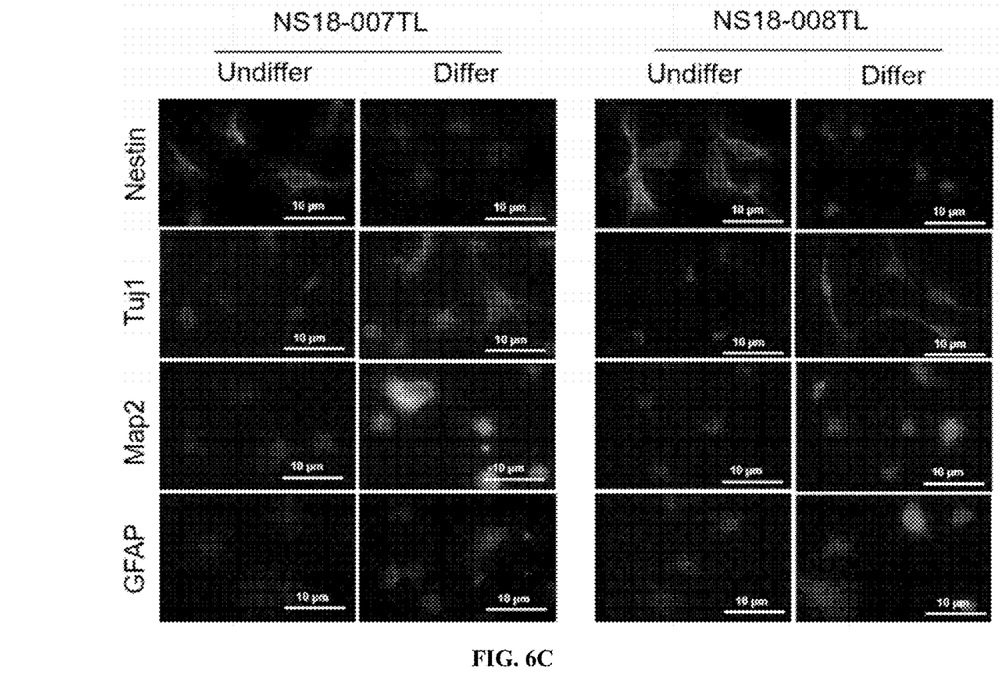
FIG. 6C shows the results of immunofluorescence staining after differentiation to confirm that neural stem cells derived from Clump type II maintain neural differentiation ability.

In addition, as a result of immunofluorescence staining, as shown in FIG. 6C, a undifferentiation marker, Nestin was strongly expressed before differentiation, but was scarcely observed after differentiation, and the expression of neuron markers, Tuj 1 and Map2, was not observed before differentiation, but observed after differentiation. An astrocyte marker, GFAP, was hardly observed before differentiation, but observed after differentiation.

This result means that the neural stem cells derived from Clump type II maintain neural stem cell characteristics.

Example 7. Confirmation of Angiogenic Effects of Neural Stem Cells Derived from Clump Type II Umbilical vein endothelial cells (HUVECs) were purchased from Promocell, and cultured using the manufacturer's exclusive medium. $1\times10^6$ of HUVECs and $1\times10^6$ of neural stem cells were mixed in 200 µL of phenol red-free Matrigel (BD), and subcutaneously transplanted into 4 to 6-week old Balbc-nu mice. After 3 to 4 days, Matrigel was removed, and then fixed with 4% PFA for 24 hours, followed by making a block. For histological analysis, hematoxylin & eosin (H&E) staining was performed. To stain new blood vessels generated in Matrigel, HUVECs and neural stem cells were subjected to immunofluorescence staining for CD31 and alpha-smooth muscle actin (a-SMA).

Figure 7A:
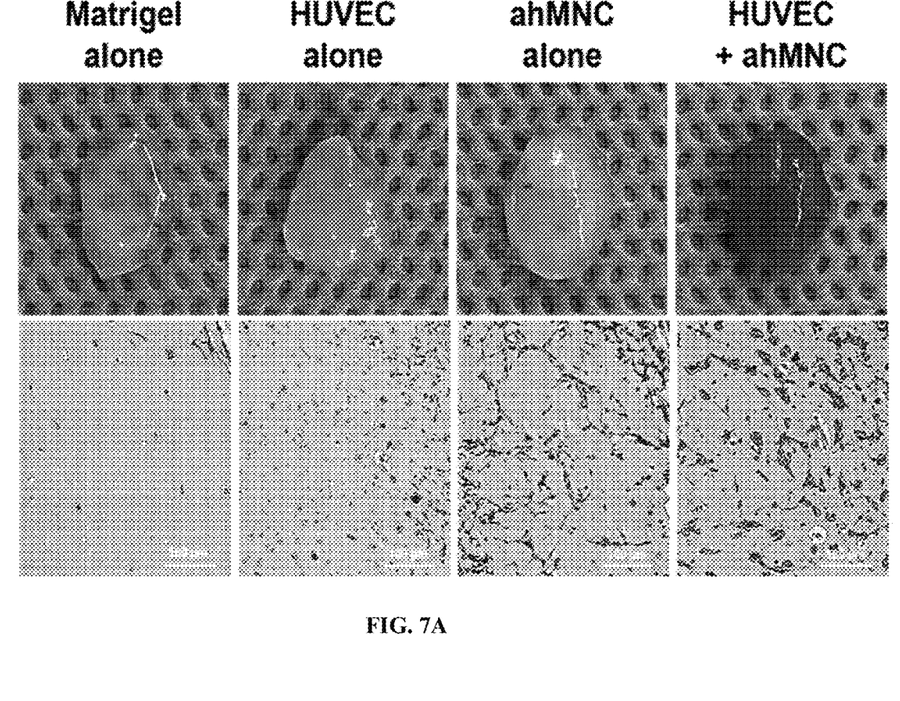
FIG. 7A shows the angiogenic ability of neural stem cells derived from Clump type II.
Figure 7B:
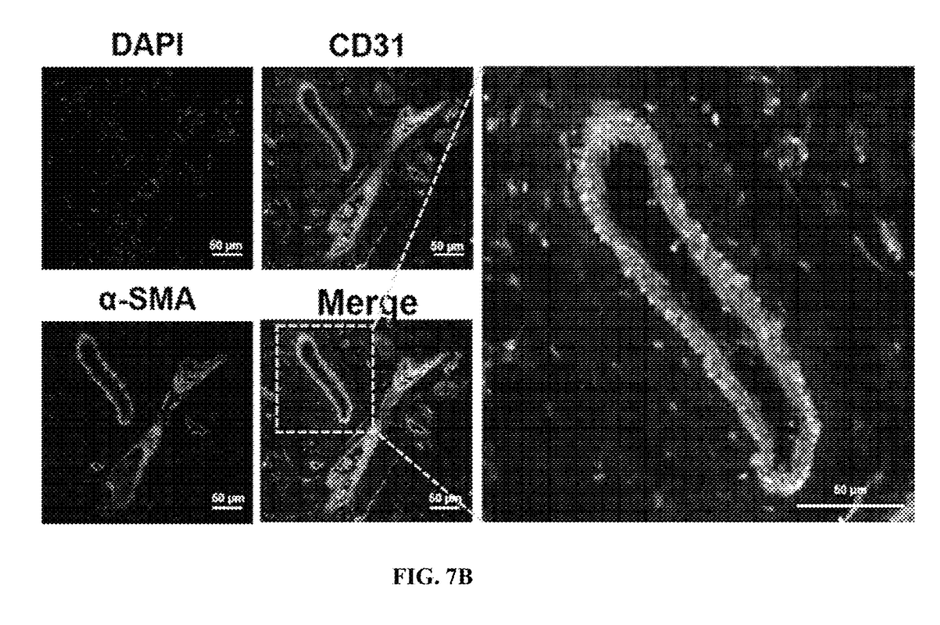
FIG. 7B shows the results of immunofluorescence staining for α-SMA and CD31 to confirm the localization of transplanted neural stem cells.

As a result, as shown in FIG. 7A, blood vessels were hardly formed by neural stem cells, but blood vessel formation was able to be confirmed when HUVECs and neural stem cells were mixed and transplanted. In addition, as shown in FIG. 7B, it was confirmed that the neural stem cells were located around a blood vessel, contributing to blood vessel formation.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

A method for isolating and culturing neural stem cells with high efficiency according to the present invention may shorten an isolation and culture time by simplifying a method of isolating and culturing neural stem cells, and increase the yield of neural stem cells. In addition, the present invention has advantages of increasing cell viability due to the shortening of an isolation and culture time, and increasing the success rate of culture of neural stem cells by obtaining a large number of cells in a short time, and thus is expected to contribute to treatment of a central nervous system disease to achieve direct or indirect neural regeneration effects using neural stem cells. In addition, the present invention is expected to be also used in the fields related to direct or indirect neural regeneration by a protein or enzyme released from neural stem cells (purification of a conditioned medium, development of an exosome, etc.).

The invention claimed is:

1. A method for isolating and culturing neural stem cells with high efficiency, comprising:
   placing brain tissue in an enzyme solution for enzyme treatment;
   physically dissociating cell clumps from the enzyme-treated brain tissue;
   separating the cell clumps by size and removing impurities; and
   performing subculture by seeding the cell clumps that have a size greater than 70 μm and less than 100 μm in a culture dish,
   wherein the method of isolating and culturing neural stem cells does not comprise isolating single cells,
   wherein the step of separating the cell clumps by size comprises the steps of:
   a) filtering the cell clumps through a 100 μm mesh and collecting the filtrate;
   b) filtering the filtrate of step a) through a 70 μm mesh; and
   c) collecting the cell clumps caught by the 70 μm mesh.

2. The method of claim 1, wherein the enzyme solution contains papain; DNase I; and D, L-cysteine.

3. The method of claim 1, wherein the brain tissue is adult brain tissue.

* * * * *